(12) United States Patent
Forsell

(10) Patent No.: US 7,407,479 B2
(45) Date of Patent: *Aug. 5, 2008

(54) INCONTINENCE TREATMENT APPARATUS WITH CONNECTION DEVICE

(76) Inventor: Peter Forsell, Aegerlstrasse 66, Zug (CH) CH-6300

( * ) Notice: Subject to any disclaimer, the term of this patent is extended or adjusted under 35 U.S.C. 154(b) by 0 days.

This patent is subject to a terminal disclaimer.

(21) Appl. No.: 10/543,630

(22) PCT Filed: Jan. 31, 2003

(86) PCT No.: PCT/SE03/00173

§ 371 (c)(1),
(2), (4) Date: Jul. 28, 2005

(87) PCT Pub. No.: WO2004/066887

PCT Pub. Date: Aug. 12, 2004

(65) Prior Publication Data

US 2006/0161041 A1    Jul. 20, 2006

(51) Int. Cl.
*A61F 2/00* (2006.01)
(52) U.S. Cl. .................................................. 600/29
(58) Field of Classification Search ............ 600/38–41, 600/29–31; 128/897–899, DIG. 25; 606/151–158, 606/201, 203
See application file for complete search history.

(56) References Cited

U.S. PATENT DOCUMENTS

| 5,449,368 A | 9/1995 | Kuzmak |
| 6,929,625 B2 * | 8/2005 | Bierman ................ 604/174 |

FOREIGN PATENT DOCUMENTS

| FR | 2 797 181 | 2/2001 |
| WO | 01/47431 | 7/2001 |
| WO | WO 01/47434 | * 7/2001 |

OTHER PUBLICATIONS

International Search Report for PCT/SE2003/000173 dated Aug. 25, 2003.

* cited by examiner

*Primary Examiner*—John P Lacyk
(74) *Attorney, Agent, or Firm*—Nixon & Vanderhye P.C.

(57) ABSTRACT

An apparatus for treating an anal or urinary incontinent patient includes an elongate adjustable constriction member adapted to extend in a loop around and constrict the patient's large intestine or urethra to close the intestinal or urethral lumen and release the large intestine or urethra to open the intestinal or urethral lumen. A connection device releasably connects the end portions of the constriction member to each other and an adjustment device adjusts the longitudinal extension of the constriction member in the loop to change the constriction of the large intestine or urethra. The connection device includes a female part and a male part fitting into the female part to lock them together. The design of the connection device facilitates laparoscopic surgery for implanting the constriction member.

14 Claims, 2 Drawing Sheets

INCONTINENCE TREATMENT APPARATUS WITH CONNECTION DEVICE

This application is the US national phase of International Application No. PCT/SE2003/000173 filed 31 Jan. 2003, which designated the U.S., the entire content of which is incorporated herein by reference.

The present invention relates to an apparatus for treating an anal or urinary incontinent patient comprising a constriction device including an elongate adjustable constriction member having first and second end portions and adapted to extend in a loop around and constrict the patient's large intestine or urethra to close the intestinal or urethral lumen and release the large intestine or urethra to open the intestinal or urethral lumen. The apparatus further comprises a connection device for releasably connecting the first and second end portions of the constriction member to each other, and an adjustment device that adjusts the longitudinal extension of the constriction member in the loop to change the constriction of the large intestine or urethra.

Anal incontinence is a widespread disease. Several kinds of sphincter plastic surgery are used today to remedy anal incontinence. There is a prior manually operated sphincter system in an initial clinical trial phase where a hydraulic sphincter system connected to an elastic reservoir (balloon) placed in the scrotum is developed. A disadvantage of this system is that thick, hard fibrosis is created around the reservoir by pump movements making the system useless sooner or later.

U.S. Pat. No. 5,593,443 discloses a hydraulic anal sphincter under both reflex and voluntary control. A pressure controlled inflatable artificial sphincter is disclosed in U.S. Pat. No. 4,222,377. WO 01/45488 discloses a hydraulically adjustable constriction device for constricting the large intestine of an anal incontinent patient.

Also urinary incontinence is a widespread problem. Many people are helped through training of the muscles in the pelvic floor but too many have severe problems with urine leakage. Many different solutions to this problem have been tried. For example, there is a prior manually operated urine incontinence treatment apparatus having an artificial hydraulic sphincter device engaging the urethra and connected to an elastic reservoir implanted in the scrotum or in the region of the labia major. A disadvantage of this prior apparatus is that over time hard fibrosis is developed around the reservoir, which may cause malfunction of pumping components. Furthermore, it is a rather complicated task to manually squeeze the elastic implanted reservoir to pump hydraulic fluid to open the sphincter device when the patient needs to urinate. In particular women can get their fingers wet. The created fibrosis will sooner or later become a hard fibroid layer, which may make it even more difficult to pump the reservoir. Yet a further disadvantage is that the use of hydraulic fluid always entails a risk of fluid leaking from implanted hydraulic components.

A prior hydraulic apparatus designed to constrict the urethra is disclosed in U.S. Pat. No. 5,520,606. A prosthetic sphincter with an inflatable cuff, which surrounds the urethra or encloses it on two sides, is disclosed in for example U.S. Pat. Nos. 4,571,749 and 4,222,377. U.S. Pat. No. 4,969,474 discloses a hydraulic method for treating both men and women with urinary incontinence problems in the same way. The apparatus of U.S. Pat. No. 4,969,474 includes a reservoir containing fluid and an inflatable compression means designed to constrict the urethra without risking tissue loss or necrosis to occur. An artificial hydraulically operated urethra sphincter employing an external magnet to achieve closure of the urethra cuff is disclosed in U.S. Pat. No. 5,562,598. WO 01/45488 discloses a hydraulically adjustable constriction device for constricting the urethra of a urinary incontinent patient.

The object of the present invention is to provide a new convenient apparatus for treating incontinence, which is easy to apply around and, if desired, easy to remove from a patient's large intestine or urethra.

This object is obtained by an apparatus of the kind presented initially characterised in that the connection device includes a female part and a male part fitting into the female part to lock them together.

In accordance with a preferred embodiment of the invention, the male part includes a shank and a head on the shank and the female part includes two jaws defining a bore for receiving the head of the male part and a passage narrower than and extending from the bore for receiving the shank of the male part, whereby the male part can be locked to the female part by laterally displacing the head and shank of the male part into the bore and passage, respectively. The jaws are formed with indentations in the bore adjacent the passage, such that the head can be displaced laterally relative to the bore into the indentations, whereby the head is prevented from being displaced out of the bore.

Other embodiments of the invention are also conceivable. For example, the male and female parts may be designed as snap fasteners or male and female pipes, which may or may not be provided with threads.

The constriction member may be non-inflatable and the adjustment device may include a motor for adjusting the non-inflatable constriction member. Alternatively, the constriction member may be a hydraulic constriction member, typically with an inflatable cavity, and the adjustment device may include a pump hydraulically connected to the hydraulic constriction member.

Generally, the adjustment device comprises a powered adjustment device, for example including a motor, preferably an electric motor. The apparatus may comprise an implantable energy-transforming device adapted to transform wireless energy emitted from outside the patient's body into an energy form suited for powering the adjustment device. Such an energy form may be electric energy for powering an electric motor of the adjustment device.

To conveniently adjust the constriction of the large intestine or urethra, the apparatus may comprise a wireless remote control for controlling the adjustment device from outside the patient's body to adjust the constriction device.

The invention also provides a method for laparoscopically implanting in a patient a constriction device of the apparatus as described above to form a restricted cross-sectional area of the patient's large intestinal or urethral lumen. The method comprises insufflating the patient's abdomen, placing at least two laparoscopic trocars in the abdomen, using a dissecting tool inserted through the laparoscopic trocar, dissecting the region of the large intestine or urethra, introducing a constriction device of the apparatus described above through the trocars, and using tools inserted in the trocars forming a loop of the constriction member of the restriction device around the large intestine or urethra in the dissected region and connecting the male and female parts to each other.

The invention also provides a method for laparoscopically removing a constriction device of the apparatus as described above applied on the large intestine or urethra of an incontinent patient. The method comprises insufflating the patient's abdomen, placing at least two laparoscopic trocars in the abdomen, and using tools inserted in the trocars releasing the male and female parts of the constriction device from each other and then removing the constriction device from the patient.

Figure 1:
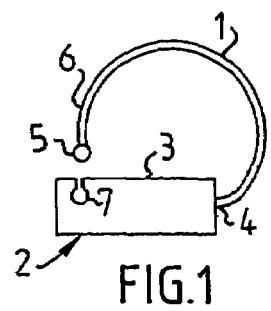
FIG. 1 is a view of the apparatus of the invention with a connection device.

FIG. 1 shows the apparatus of the present invention including a constriction device having an elongated constriction member 1 to be formed into a closed loop around an anal incontinent patient's rectum. An adjustment device 2 includes an elongate housing 3 connected to an end portion 4 of the constriction member 1. There is a connection device in the form of a male part 5 on another end portion 6 of the constriction member 1 and a female part 7 formed on the housing 3. (Alternatively, the male part 5 may be provided on the housing 3 and the female part 7 may be formed on the end portion 6.)

Figure 2:
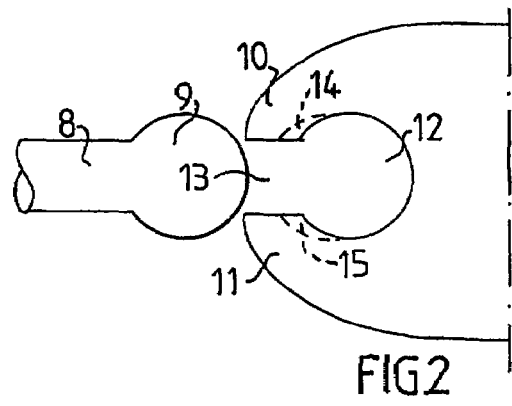
FIG. 2 is a schematic view of the connection device in an unlocked state.
Figure 3:
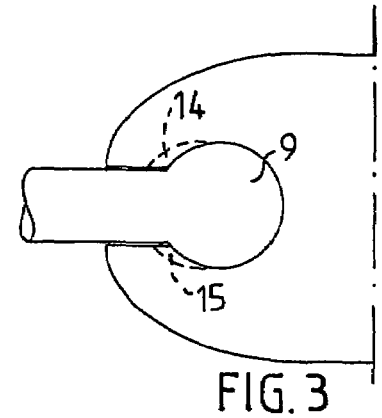
FIG. 3 is a schematic view of the connection device in a pre-locked state.
Figure 4:
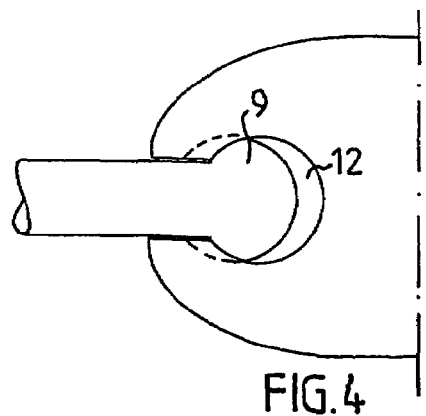
FIG. 4 is a schematic view of the connection device in a final locked state.

With reference to FIGS. 2-4, the male part 5 has a shank 8 and a spherical head 9 on the shank 8 and the female part 7 has two jaws 10,11 defining a circular bore 12 for receiving the head 9 and a passage 13 narrower than and extending from the bore 12 for receiving the shank 8. As appears from FIG. 3 the male part 5 can be pre-locked to the female part 7 by laterally displacing the head 9 and shank 8 into the bore 12 and passage 13, respectively. The jaws 10,11 are formed with spherical segment indentations 14,15 complementary to the spherical head 9. The indentations 14,15 are located in the bore 12 adjacent the passage 13. As appears from FIG. 4 the male part 5 can be finally locked to the female part 7 by displacing the head 9 laterally relative to the bore 12 into the indentations 14,15. The pressure that the rectum constantly exerts on the constriction member when the apparatus is implanted ensures that the connection device 5, 7 is kept in a locked state.

In case the apparatus should be removed from the patient, the surgeon may conveniently use laparoscopic surgery to introduce a suitable tool into the patient's abdomen to release the head 9 from the jaws 11,11 and displace the head 9 out of the bore 12.

Figure 5:
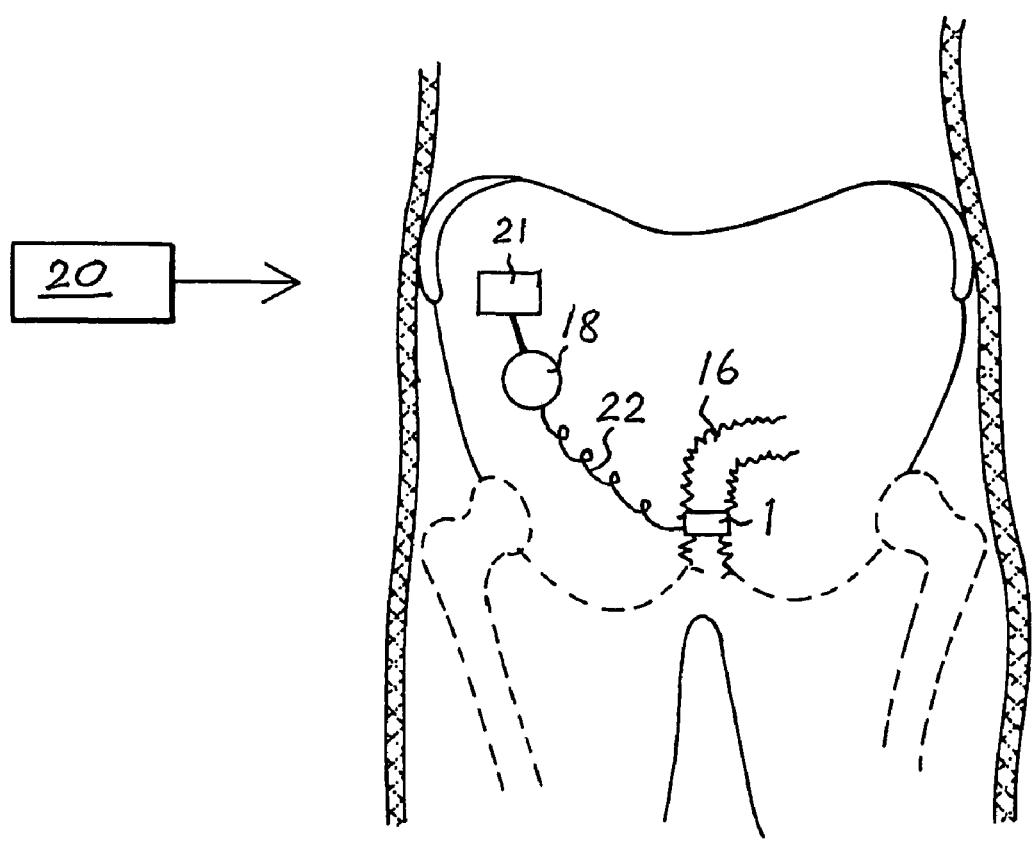
FIG. 5 illustrates the apparatus of the invention implanted in an anal incontinent patient.

FIG. 5 illustrates the construction device the embodiment shown in FIGS. 1-4 applied on the rectum 16 of an anal incontinent patient. The elongate constriction member 1 and housing 3 of the constriction device extend in a loop around and constricts the rectum to normally close the rectal lumen. A rechargeable electric power supply 18 is implanted in the patient to supply electric energy for the operation of the adjustment device 2. When the patient desires to relieve himself or herself, the patient uses an external remote control 20 to control the adjustment device 2 to adjust the constriction member 1 to release the rectum, whereby the patient may defecate.

The remote control 20 transmits signals that are received by a combined control and energy-transforming unit 21 subcutaneously implanted in the patient. The unit 21 is electrically connected to the electric power supply 18 and transforms the energy of the signals into an electric current that is used for charging the electric power supply 18. For example, the signals may include electromagnetic waves and the unit 21 may include an electric p-n junction element that transforms the wireless energy into an electric current.

A resilient insulated electric wire 22 connects the power supply 18 and an electric motor of the adjustment device 2 contained in the housing 3. The electric wire 22 extends helically between the power supply 18 and housing 3, in order to permit the electric wire 22 to be temporarily extended when movements of the rectum 16 occur, so that the risk of breaking the electric wire 22 is eliminated.

The invention claimed is:

1. An apparatus for treating an anal or urinary incontinent patient comprises a constriction device implantable in the patient for engaging the patient's large intestine or urethra, the constriction device including an adjustable constriction member for constricting the patient's large intestine or urethra to close the intestinal or urethral lumen and release the large intestine or urethra to open the intestinal or urethral lumen, the constriction member having first and second end portions, a connection device for releasably connecting the first and second end portions of the constriction member to each other, and an implantable adjustment device that adjusts the constriction member to change the constriction of the large intestine or urethra, the connection device including a female part and a male part for insertion into the female part, the male part comprising a shank and a spherical head on the end of the shank and the female part comprising two jaws with an open front and two open sides, the jaws defining a semi-circular bore and a passage narrower than and extending from the bore to the open front of the jaws for removably receiving the spherical head and the shank, respectively, the bore being larger in volume than the spherical head of the male part, the male part being locked to the female part, after the spherical head and shank have been inserted through one of the open sides of the jaws into the bore and passage, respectively, by displacing the spherical head within the semi-circular bore in the direction of the passage and the shank along the passage away from the bore and towards the open front of the jaws, whereupon the longitudinal extension of the constriction member in the loop can be adjusted to constrict the large intestine or urethra without the male part separating from the female part.

2. An apparatus according to claim 1, wherein the jaws are formed with indentations in the semi-circular bore adjacent to the passage fitting the spherical head of the male part, such that the head can be displaced relative to the bore into the indentations to lock the male and female parts to each other.

3. An apparatus according to claim 1, wherein the constriction member is non-inflatable.

4. An apparatus according to claim 3, wherein the adjustment device comprises a motor.

5. An apparatus according to claim 1, wherein the constriction member comprises a hydraulic constriction member and the adjustment device comprises a pump hydraulically connected to the hydraulic constriction member.

6. An apparatus according to claim 1, wherein the adjustment device comprises a powered adjustment device and further comprising an implantable energy transforming device for transforming wireless energy emitted from outside the patient's body into an energy form suited for powering the adjustment device.

7. An apparatus according to claim 1, further comprising a wireless remote control for controlling the adjustment device to adjust the constriction device.

8. An apparatus for treating an anal or urinary incontinent patient comprises a constriction device implantable in the patient for engaging the patient's large intestine or urethra, the constriction device including an elongate adjustable constriction member adapted to extend in a loop around and constrict the patient's large intestine or urethra to close the intestinal or urethral lumen and release the large intestine or urethra to open the intestinal or urethral lumen, the constriction member having first and second end portions, a connection device for releasably connecting the first and second end portions of the constriction member to each other, and an implantable adjustment device that adjusts the longitudinal extension of the constriction member in the loop to change the constriction of the large intestine or urethra, the connection device including a female part and a male part for insertion into the female part, the male part comprising a shank and a head on the end of the shank and the female part comprising two jaws with an open front and two open sides, the jaws defining a bore and a passage narrower than and extending from the bore to the open front of the jaws for removably receiving the head and the shank, respectively, the bore being larger in volume than the head of the male part, the male part being locked to the female part, after the head and shank have been inserted through one of the open sides of the jaws into the bore and passage, respectively, by displacing the head within the bore in the direction of the passage and the shank along the passage away from the bore and towards the open front of the jaws, the jaws being formed with indentations in the bore adjacent the passage fitting the head of the male part, such that the head can be displaced within the bore into the indentations to lock the male and female parts to each other, whereupon the longitudinal extension of the constriction member in the loop can be adjusted to constrict the large intestine or urethra without the male part separating from the female part.

9. An apparatus according to claim 8, wherein the constriction member is non-inflatable.

10. An apparatus according to claim 9, wherein the adjustment device comprises a motor.

11. An apparatus according to claim 8, wherein the constriction member comprises a hydraulic constriction member and the adjustment device comprises a pump hydraulically connected to the hydraulic constriction member.

12. An apparatus according to claim 8, wherein the adjustment device comprises a powered adjustment device and further comprising an implantable energy transforming device adapted to transform wireless energy emitted from outside the patient's body into an energy form suited for powering the adjustment device.

13. An apparatus according to claim 8, further comprising a wireless remote control for controlling the adjustment device to adjust the constriction device.

14. An apparatus according to claim 8, wherein the head of the male part is spherical and the two jaws of the female part define a semi-spherical bore for receiving the spherical head of the male part.

* * * * *